(12) United States Patent
Charles (10) Patent No.: US 10,064,549 B2
(45) Date of Patent: Sep. 4, 2018

(54) BINOCULAR EN FACE OPTICAL COHERENCE TOMOGRAPHY IMAGING

(71) Applicant: NOVARTIS AG, Basel (CH)

(72) Inventor: Steven T. Charles, Memphis, TN (US)

(73) Assignee: Novartis AG, Basel (CH)

( * ) Notice: Subject to any disclaimer, the term of this patent is extended or adjusted under 35 U.S.C. 154(b) by 54 days.

(21) Appl. No.: 14/942,745

(22) Filed: Nov. 16, 2015

(65) Prior Publication Data
US 2017/0135573 A1    May 18, 2017

(51) Int. Cl.
*A61B 3/14* (2006.01)
*A61B 3/10* (2006.01)
*A61B 3/13* (2006.01)
*A61B 3/00* (2006.01)

(52) U.S. Cl.
CPC ............ *A61B 3/102* (2013.01); *A61B 3/0025* (2013.01); *A61B 3/0058* (2013.01); *A61B 3/132* (2013.01)

(58) Field of Classification Search
CPC ........... A61B 3/14; A61B 3/0025; A61B 3/12; A61B 3/102; A61B 3/113; A61B 3/0058; A61B 3/1225; A61B 3/1025; A61B 3/145; A61B 3/0041; A61B 3/0008; A61B 3/0091; A61B 3/1015; A61B 3/103; A61B 3/117; A61B 3/112; A61B 3/152; A61B 3/01; A61B 3/1005
USPC ........ 351/206, 208, 205, 221, 207, 219, 216
See application file for complete search history.

(56) References Cited

U.S. PATENT DOCUMENTS

| | | | | |
|---|---|---|---|---|
| 8,820,931 B2 * | 9/2014 | Walsh | ..................... | A61B 3/102 351/206 |
| 2011/0299034 A1 * | 12/2011 | Walsh | ..................... | A61B 3/102 351/206 |
| 2012/0184846 A1 * | 7/2012 | Izatt | ................... | G02B 21/0012 600/425 |

* cited by examiner

*Primary Examiner* — Thomas K Pham
*Assistant Examiner* — Sharrief Broome
(74) *Attorney, Agent, or Firm* — Baker Botts L.L.P.

(57) ABSTRACT

Binocular en face OCT imaging during ophthalmic surgery may be performed with an OCT scanning controller that interfaces to an OCT scanner used with a surgical microscope. The OCT scanner may generate left and right sample beams, and receive left and right measurement beams, respectively, to generate left and right scan data. The OCT scanning controller may process the left and right scan data to generate left and right en face images for respective viewing from binoculars in the surgical microscope to obtain an intraoperative stereoscopic en face view of interior portions of the eye.

18 Claims, 5 Drawing Sheets

BINOCULAR EN FACE OPTICAL COHERENCE TOMOGRAPHY IMAGING

BACKGROUND

Field of the Disclosure

The present disclosure relates to ophthalmic surgery, and more specifically, to binocular en face optical coherence tomography (OCT) imaging.

Description of the Related Art

In ophthalmology, eye surgery, or ophthalmic surgery, saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Ophthalmic surgery is performed on the eye and accessory visual structures. More specifically, vitreoretinal surgery encompasses various delicate procedures involving internal portions of the eye, such as the vitreous humor and the retina. Different vitreoretinal surgical procedures are used, sometimes with lasers, to improve visual sensory performance in the treatment of many eye diseases, including epimacular membranes, diabetic retinopathy, vitreous hemorrhage, macular hole, detached retina, and complications of cataract surgery, among others.

During vitreoretinal surgery, an ophthalmologist typically uses a surgical microscope to view the fundus through the cornea, while surgical instruments that penetrate the sclera may be introduced to perform any of a variety of different procedures. The surgical microscope provides imaging and optionally illumination of the fundus during vitreoretinal surgery. The patient typically lies supine under the surgical microscope during vitreoretinal surgery and a speculum is used to keep the eye exposed. Depending on a type of optical system used, the ophthalmologist has a given field of view of the fundus, which may vary from a narrow field of view to a wide field of view that can extend to peripheral regions of the fundus.

In addition to viewing the fundus, surgical microscopes may be equipped with optical coherence tomography (OCT) scanners to provide additional information about portions of eye tissue involved with the vitreoretinal surgery. The OCT scanner may enable imaging below a visible surface of the eye tissue during vitreoretinal surgery.

SUMMARY

In one aspect, a disclosed method is for performing ophthalmic surgery using binocular en face OCT imaging. The method may include viewing an interior portion of an eye of a patient using a surgical microscope and an ophthalmic lens to generate an optical image of the interior portion of the eye. In the method, the surgical microscope may include a left ocular and a right ocular. The method may further include sending a command to an OCT scanning controller coupled to the surgical microscope for binocular en face viewing of the interior portion of the eye. In the method, the OCT scanning controller is in communication with an OCT scanner. In the method, the OCT scanner is enabled for transmitting a left sample beam via a left optical path and a right sample beam via a right optical path to the interior portion of the eye, receiving a left measurement beam via the left optical path to generate left scan data, and receiving a right measurement beam via the right optical path to generate right scan data. In the method, the OCT scanning controller is enabled for receiving the right scan data and the left scan data from the OCT scanner, generating a left en face image from the left scan data, generating a right en face image from the right scan data, causing the left en face image to be displayed in the left ocular, and causing the right en face image to be displayed in the right ocular.

In any of the disclosed embodiments of the method, the transmitting may further include reciprocating, by the OCT scanner, an optical mirror from a common optical source to generate the left sample beam and the right sample beam in an alternating manner in time. In any of the disclosed embodiments of the method, the receiving the left measurement beam and the receiving the right measurement beam may further include receiving, by the OCT scanner, the left measurement beam and the right measurement beam in the alternating manner in time.

In any of the disclosed embodiments of the method, the transmitting may further include splitting, by the OCT scanner, light from a common optical source to simultaneously transmit the left sample beam and the right sample beam. In any of the disclosed embodiments of the method, the receiving the left measurement beam and the receiving the right measurement beam may further include receiving, by the OCT scanner, the left measurement beam using a first detector, and receiving, by the OCT scanner, the right measurement beam using a second detector.

In any of the disclosed embodiments of the method, the right en face image and the left en face image may exhibit angular diversity with respect to the interior portion of the eye.

In any of the disclosed embodiments of the method, the right en face image and the left en face image may be viewable together to visualize a 3-dimensional (3D) en face view. In any of the disclosed embodiments of the method, the 3D en face view depicts a selected depth from the left scan data and the right scan data. In any of the disclosed embodiments of the method, the 3D en face view depicts a selected tissue layer from the left scan data and the right scan data.

In a further aspect, an OCT scanning controller is for binocular en face OCT imaging during ophthalmic surgery. The OCT scanning controller may include a processor having access to memory media storing instructions executable by the processor. In the OCT scanning controller, the instructions may be executable by the processor for receiving a first command for binocular en face OCT from an interior portion of an eye of a patient and for sending a second command to an OCT scanner to initiate binocular en face OCT via a surgical microscope and an ophthalmic lens. In conjunction with the OCT scanning controller, the surgical microscope and the ophthalmic lens may also be used to generate an optical image of the interior portion of the eye, while the surgical microscope may include a left ocular and a right ocular. In conjunction with the OCT scanning controller, the OCT scanner is enabled for transmitting a left sample beam via a left optical path and a right sample beam via a right optical path to the interior portion of the eye, receiving a left measurement beam via the left optical path to generate left scan data, and receiving a right measurement beam via the right optical path to generate right scan data. The OCT scanning controller may further include instructions for receiving the right scan data and the left scan data from the OCT scanner, generating a left en face image from the left scan data, generating a right en face image from the right scan data, causing the left en face image to be displayed in the left ocular, and causing the right en face image to be displayed in the right ocular.

In any of the embodiments of the OCT scanning controller, the transmitting may further include the OCT scanner being enabled for reciprocating an optical mirror from a common optical source to generate the left sample beam and the right sample beam in an alternating manner in time. In any of the embodiments of the OCT scanning controller, the receiving the left measurement beam and the receiving the right measurement beam may include the OCT scanner being enabled for receiving the left measurement beam and the right measurement beam in the alternating manner in time.

In any of the embodiments of the OCT scanning controller, the transmitting may include the OCT scanner being enabled for splitting light from a common optical source to simultaneously transmit the left sample beam and the right sample beam. In any of the embodiments of the OCT scanning controller, the receiving the left measurement beam and the receiving the right measurement beam may include the OCT scanner being enabled for receiving the left measurement beam using a first detector, and receiving the right measurement beam using a second detector.

In any of the embodiments of the OCT scanning controller, the right en face image and the left en face image exhibit angular diversity with respect to the interior portion of the eye.

In any of the embodiments of the OCT scanning controller, the right en face image and the left en face image are viewable together to visualize a 3-dimensional (3D) en face view. In any of the embodiments of the OCT scanning controller, the 3D en face view depicts a selected depth from the left scan data and the right scan data. In any of the embodiments of the OCT scanning controller, the 3D en face view depicts a selected tissue layer from the left scan data and the right scan data.

Additional disclosed embodiments include an OCT scanner, a surgical microscope, and an image processing system.

BRIEF DESCRIPTION OF THE DRAWINGS

For a more complete understanding of the present disclosure, reference is now made to the following description, taken in conjunction with the accompanying drawings, in which.

DESCRIPTION OF PARTICULAR EMBODIMENTS

In the following description, details are set forth by way of example to facilitate discussion of the disclosed subject matter. It should be apparent to a person of ordinary skill in the field, however, that the disclosed embodiments are exemplary and not exhaustive of all possible embodiments.

As used herein, a hyphenated form of a reference numeral refers to a specific instance of an element and the un-hyphenated form of the reference numeral refers to the collective element. Thus, for example, device '12-1' refers to an instance of a device class, which may be referred to collectively as devices '12' and any one of which may be referred to generically as a device '12'.

As noted above, during vitreoretinal surgery a surgeon may view the fundus of an eye of a patient using a surgical microscope, for example, in conjunction with an ophthalmic lens for viewing through the cornea, such as a contact or non-contact lens. In order to perform any of a variety of surgical procedures, the surgeon may desire to optically scan certain portions of the fundus to generate profile depth scans of the corresponding eye tissue, such as by using an OCT scanner. The profile depth scans may reveal information about eye tissue that is not readily visible from optical images generated by the surgical microscope. The profile depth scans may be point scans (A-scan), line scans (B-scan), or area scans (C-scan). An image from a B-scan will image the depth of eye tissue along a line, while a C-scan results in 3-dimensional (3D) data that can be sectioned to provide various views, including an en face view from the optical view perspective, but which can be generated at various depths and for selected tissue layers.

Although OCT scanners have been integrated with the optics of surgical microscopes having binocular optics, OCT systems (comprising scanners and scanning controllers) typically do not support true binocular optics, which involves the acquisition of two distinct images taken from slightly different points of view to enable stereoscopic imaging with enhanced depth perception. The binocular images enable the human mind to perceive depth and human visual processing improves signal-to-noise ratio when presented with a stereo pair of noisy images. Furthermore, OCT is subject to speckle patterns because of the diffuse reflection that takes place to generate OCT measurement beams and speckle is a known source of noise in OCT scan data. Because binocular imaging results from two images having angular diversity, binocular en face OCT imaging also reduces speckle by averaging out the random speckle patterns. Such improvements resulting from binocular en face OCT imaging may provide significant benefits for vitreoretinal surgeons and may result in reduced errors and associated complications, among other benefits.

The present disclosure relates to methods and systems for binocular en face OCT imaging. The methods and systems for binocular en face OCT imaging during vitreoretinal surgery disclosed herein may provide natural stereo information to facilitate intraoperative surgical manipulation with greater ease and fewer potential errors. The methods and systems for binocular en face, OCT imaging during vitreoretinal surgery disclosed herein may further enable the surgeon to view OCT images with less noise and greater clarity due to improved perceived signal-to-noise in the image data as well as due to speckle reduction as a result of angular diversity of the two images.

As will be described in further detail, binocular en face, volumetric (3D) OCT imaging during vitreoretinal surgery is performed using an OCT scanning controller that is integrated with the OCT scanner and the surgical microscope. The OCT scanning controller may send commands to control operation of the OCT scanner, including for binocular en face OCT viewing of the interior portion of the eye of a patient. In various embodiments and implementations, as described herein, the OCT scanner may transmit a left sample beam via a left optical path and a right sample beam via a right optical path to the interior portion of the eye. The OCT scanner may receive a left measurement beam via the left optical path to generate left scan data, and receive a right measurement beam via the right optical path to generate right scan data. After receiving the right scan data and the left scan data, the OCT scanning controller may generate left and right en face images and cause the images to be displayed, respectively, in a left and right ocular of the stereomicroscope.

Figure 1:
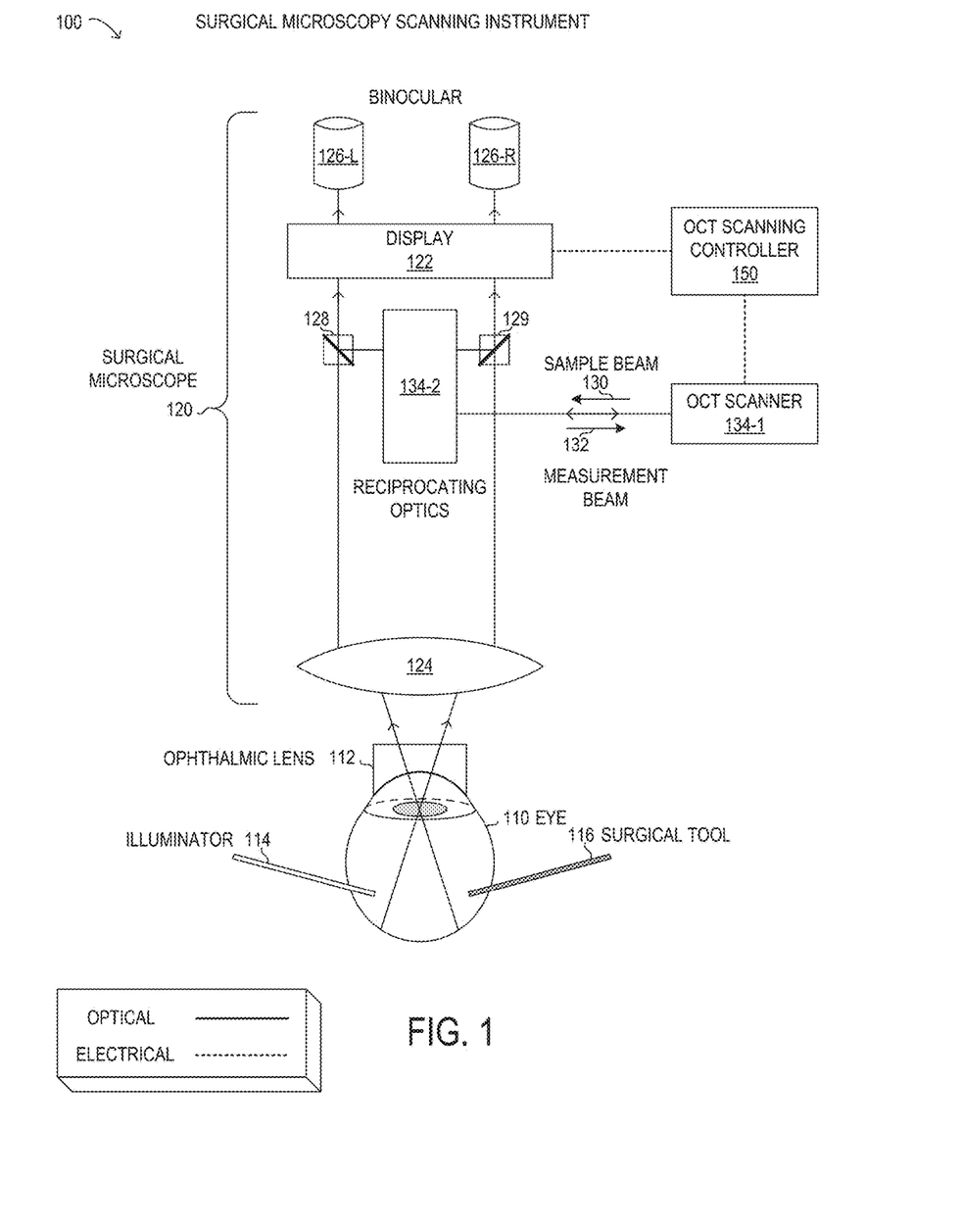
FIG. 1 is a block diagram of selected elements of an embodiment of a surgical microscopy scanning instrument.

Referring now to the drawings, FIG. 1 is a block diagram showing a surgical microscopy scanning instrument 100. Instrument 100 is not drawn to scale but is a schematic representation. As will be described in further detail, instrument 100 may be used during vitreoretinal surgery to view and analyze a human eye 110. As shown, instrument 100 includes surgical microscope 120, scanning controller 150, and OCT scanner 134-1 with reciprocating optics 134-2. Also shown in FIG. 1 are ophthalmic lens 112, as well as surgical tool 116 and illuminator 114.

As shown, surgical microscope 120 is depicted in schematic form to illustrate optical functionality. It will be understood that surgical microscope 120 may include various other electronic and mechanical components, in different embodiments. Accordingly, objective 124 may represent a selectable objective to provide a desired magnification or field of view of the fundus. Objective 124 may receive light from the fundus of eye 110 via ophthalmic lens 112 that rests on a cornea of eye 110. It is noted that various types of ophthalmic lenses 112 may be used with surgical microscope 120, including contact lenses and non-contact lenses. To perform vitreoretinal surgery, various tools and instruments may be used, including tools that penetrate the sclera, represented by surgical tool 116. Illuminator 114 may be a special tool that provides a light source from within the fundus of eye 110.

In FIG. 1, surgical microscope 120 is shown with a binocular arrangement with two distinct but substantially equal light paths that enable viewing with binoculars 126 that comprise a left ocular 126-L and a right ocular 126-R. From objective 124, a left light beam may travel through left partial mirror 128, from where left ocular 126-L receives the left optical image. Also from objective 124, a right light beam may travel through right partial mirror 129, from where right ocular 126-R receives the right optical image. Display 122 may represent an opto-electronic component, such as an image processing system that receives the left and right optical images, as well as data from OCT scanning controller 150, and generates image output for left ocular 126-L and right ocular 126-R, respectively. In some embodiments, display 122 includes miniature display devices that output images to binoculars 126 for viewing by the user.

Additionally, OCT scanner 134-1 with reciprocating optics 134-2 are integrated with surgical microscope, and may be collectively referred to as OCT scanner 134. In the embodiment depicted in FIG. 1, OCT scanner 132-1 includes a single light source for sample beam 130, which is directed to reciprocating optics 134-2. Reciprocating optics 134-2 includes optical components for redirecting sample beam 130 in an alternating manner to left partial mirror 128 and right partial mirror 129. Reciprocating optics 134-2 may be implemented using various means, such as with an optical flat mirror that is rotated at a certain frequency, for example greater than about 25 Hz, or up to about 100 Hz, to alternately direct sample beam 130 along the left and right optical paths into eye 110. In some embodiments, reciprocating optics 134-2 may be implemented using a micro-electro-mechanical system (MEMS) actuator to redirect sample beam 130 along the left and right optical paths into eye 110. As sample beam 130 is directed to either left partial mirror 128 or right partial mirror 129, measurement beam 132 is synchronously captured by a single detector at OCT scanner 134-1, which generates left scan data and right scan data. OCT scanner 134-1 sends the left scan data and the right scan data to OCT scanning controller 150, which then generates a left en face image and a right en face image for binocular viewing. It is noted that the en face binocular images generated by OCT scanning controller 150 may show any desired depth or any specific tissue layer identified in the scan data. Thus, as shown, OCT scanner 134 uses temporal modulation of sample beam 130 with a single light source and a single detector to acquire left and right binocular OCT images for stereoscopic viewing.

As shown in FIG. 1, OCT scanner 134-1 may control output of sample beam 130 and may receive measurement beam 132 that is reflected back in response to photons of sample beam 130 interacting with tissue in eye 110. OCT scanner 134-1 may also be enabled to control reciprocating optics 134-2, as discussed above to generate left and right binocular scan data, and to move sample beam 130 to a selected location, such as a location in eye 110 indicated by the user. It is noted that OCT scanner 134 may represent various types of OCT instruments and configurations, as desired, such as but not limited to time domain OCT (TD-OCT) and frequency domain OCT (FD-OCT) and swept source OCT. In particular, the scan data generated by OCT scanner 134 may include two-dimensional (2D) scan data of a line scan and three-dimensional (3D) scan data for an area scan. The scan data may represent a depth profile of the scanned tissue that enables imaging below a visible surface within the fundus of eye 110.

In FIG. 1, OCT scanning controller 150 may have an electrical interface with display 122, for example, for outputting display data. In this manner, OCT scanning controller 150 may output a display image to display 122 that is viewed at binoculars 126. Because the electrical interface between display 122 and OCT scanning controller 150 may support digital image data, OCT scanning controller 150 may perform image processing in real-time with relatively high frame refresh rates, such that a user of surgical microscope 120 may view the selected portion of eye 110 in real-time while OCT scanning is performed. Display 122 may be implemented as a liquid crystal display screen, a computer monitor, a television or the like. Display 122 may comply with a display standard for the corresponding type of display, such as video graphics array (VGA), extended graphics array (XGA), digital visual interface (DVI), high-definition multimedia interface (HDMI), DisplayPort, etc.

With the binocular arrangement of surgical microscope 120 in FIG. 1, an imaging system (not shown) may receive a portion of the left or right light beam to independently process, display, store, and otherwise manipulate light beams and image data. Accordingly, the imaging system may represent any of a variety of different kinds of imaging systems, as desired. Furthermore, an external display (not shown) may output similar images as display 122, but may represent a stand-alone monitor for viewing by various personnel during vitreoretinal surgery.

In operation of instrument 100, the user may view the fundus of eye 110 using binoculars 126 while vitreoretinal surgery is performed on eye 110. The user may provide user input to OCT scanning controller 150 to initiate an OCT scan. OCT scanning controller 150 may, in turn, communicate with OCT scanner 134 to control scanning operations and perform a real-time OCT scan to generate left and right binocular scan data, as described above. The left and right scan data may be processed by OCT scanning controller 150 to generate a left en face image displayed in left ocular 126-L and a right en face image displayed in right ocular 126-R. It is noted that the binocular en face OCT imaging may be performed continuously in real-time to generate video signals viewable at binoculars 126.

Figure 2:
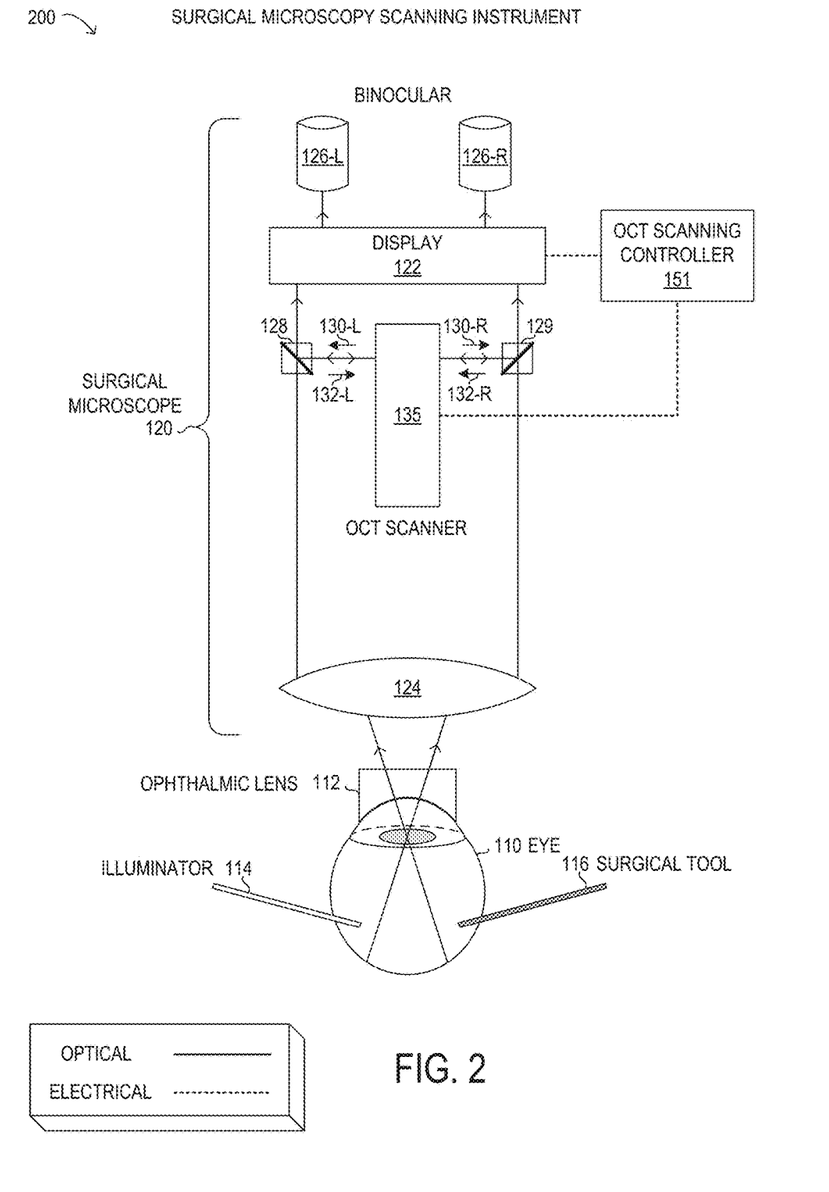
FIG. 2 is a block diagram of selected elements of an embodiment of a surgical microscopy scanning instrument.

Referring now to FIG. 2 a block diagram showing a surgical microscopy scanning instrument 200 is shown. Instrument 200 is not drawn to scale but is a schematic representation. As will be described in further detail, instrument 200 is a similar embodiment to instrument 100 in FIG. 1 for binocular en face OCT imaging during vitreoretinal surgery to view and analyze eye 110. Accordingly, the description of various common elements in FIG. 2 from FIG. 1 is not repeated below for clarity. In FIG. 2, OCT scanning controller 151 may be similar to OCT scanning controller 150 in FIG. 1 except as described below with regard to operation of an OCT scanner 135.

Specifically, in FIG. 2, instead of OCT controller 134-1 with reciprocating optics 134-2 using the common light source and the common detector, as described above with respect to FIG. 1, surgical microscopy scanning instrument 200 includes OCT scanner 135 having two separate OCT beams that are directed to left partial mirror 128 and right partial mirror 129, respectively, as shown.

In one embodiment, OCT scanner 135 includes two independent OCT scanners, with separate light sources and separate detectors (not shown). For example, OCT scanner 135 may include a first OCT scanner that generates right sample beam 130-R from a first light source and a first OCT detector that receives right measurement beam 132-R in response, and a second OCT scanner that generates left sample beam 130-L from a second light source and a second OCT detector that receives left measurement beam 132-L in response. It is noted that the use of two independent light sources in OCT scanner 135 may prevent speckle reduction in the resulting left and right en face images, because angular diversity is not given.

In another embodiment, OCT scanner 135 includes a single light source and two independent detectors (not shown). The single light source may be split using an optical splitter to simultaneously generate left sample beam 130-L and right sample beam 130-R. In such an implementation, OCT scanner 135 may include a first OCT detector that receives right measurement beam 132-R and a second OCT detector that receives left measurement beam 132-L. When OCT scanner 135 uses a single light source that is bifurcated into left sample beam 130-L and right sample beam 130-R, angular diversity is given and speckle reduction may be observed in the resulting binocular en face image.

Thus, OCT scanner 135 in FIG. 2 may simultaneously generate the right scan data and the left scan data for further processing by OCT scanning controller 151, in a substantially similar manner as described above for OCT scanning controller (see FIG. 1), to generate the right en face image and the left en face image.

Modifications, additions, or omissions may be made to surgical microscopy scanning instruments 100 and 200 without departing from the scope of the disclosure. The components and elements of surgical microscopy scanning instruments 100 and 200, as described herein, may be integrated or separated according to particular applications. Surgical microscopy scanning instruments 100 and 200 may be implemented using more, fewer, or different components in some embodiments.

Figure 3:
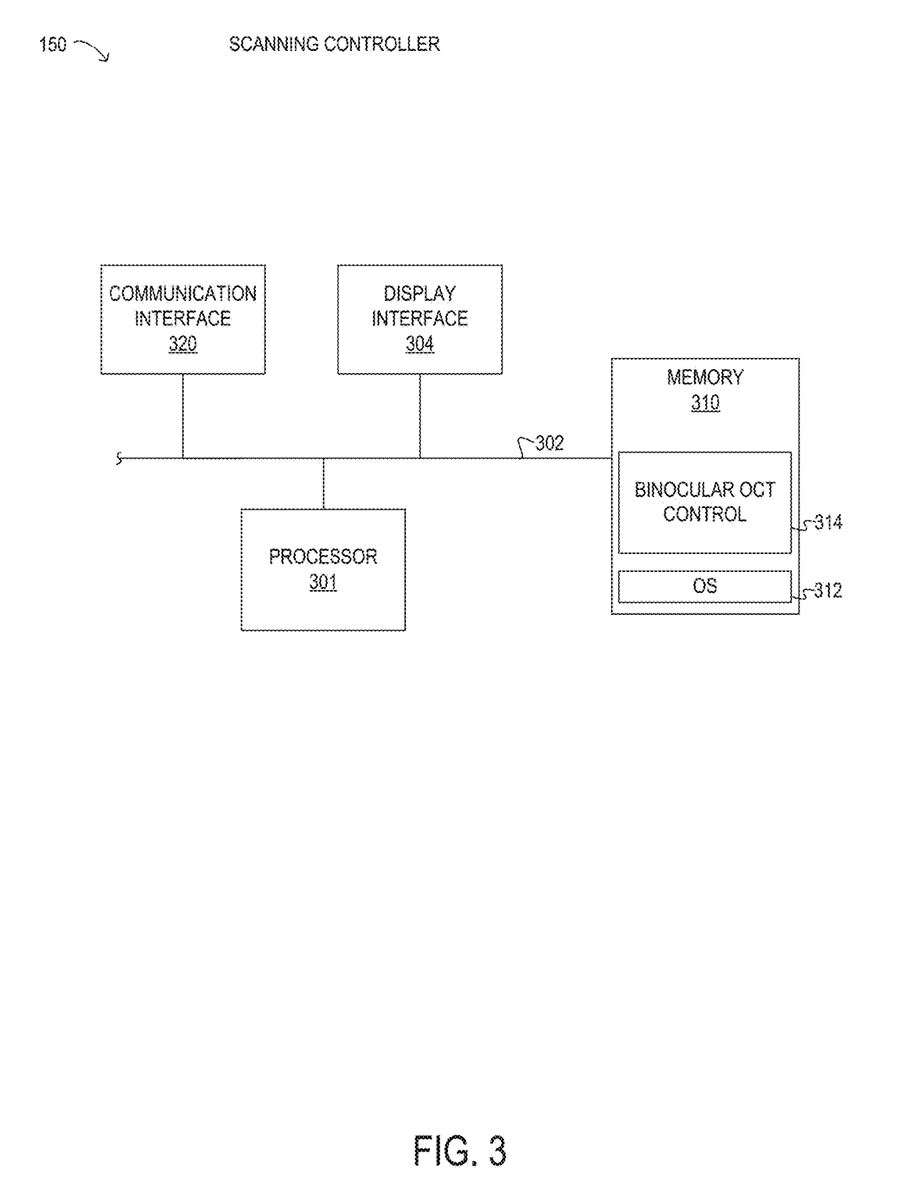
FIG. 3 is a block diagram of selected elements of an embodiment of an OCT scanning controller.

Referring now to FIG. 3, a block diagram illustrating selected elements of an embodiment of OCT scanning controller 150, described above with respect to FIGS. 1 and 2, is presented. In the embodiment depicted in FIG. 3, OCT scanning controller 150 includes processor 301 coupled via shared bus 302 to memory media collectively identified as memory 310.

OCT scanning controller 150, as depicted in FIG. 3, further includes communication interface 320 that can interface OCT scanning controller 150 to various external entities, such as OCT scanner 134, among other devices. In some embodiments, communication interface 320 is operable to enable OCT scanning controller 150 to connect to a network (not shown in FIG. 3). In embodiments suitable for binocular en face OCT imaging during vitreoretinal surgery, OCT scanning controller 150, as depicted in FIG. 3, includes display interface 304 that connects shared bus 302, or another bus, with an output port for one or more displays, such as display 122 or an external display.

In FIG. 3, memory 310 encompasses persistent and volatile media, fixed and removable media, and magnetic and semiconductor media. Memory 310 is operable to store instructions, data, or both. Memory 310 as shown includes sets or sequences of instructions, namely, an operating system 312, and a binocular OCT control application 314. Operating system 312 may be a UNIX or UNIX-like operating system, a Windows® family operating system, or another suitable operating system.

Figure 4:
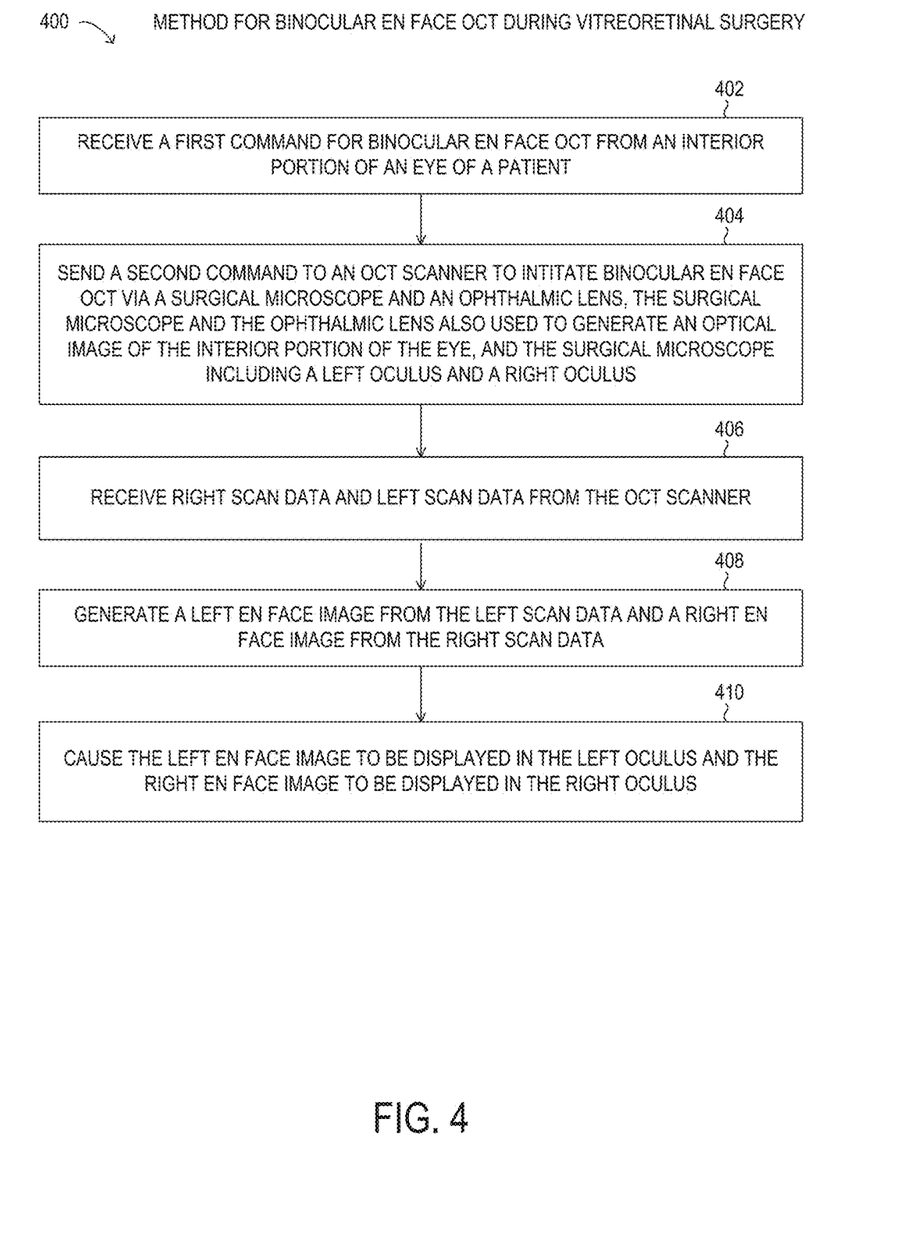
FIG. 4 is a flow chart of selected elements of a method for binocular en face OCT during vitreoretinal surgery.

Referring now to FIG. 4, a flow chart of selected elements of an embodiment of a method 400 for binocular en face OCT imaging during vitreoretinal surgery, as described herein, is depicted in flowchart form. Method 400 describes steps and procedures that the user may perform while operating surgical microscopy scanning instrument 100 and 200 to view the fundus of an eye and performing surgical procedures based on the view of the fundus. It is noted that certain operations described in method 400 may be optional or may be rearranged in different embodiments. Method 400 may be performed by a surgeon or by other medical personnel.

Method 400 may begin, at step 402, by receiving a first command for binocular en face OCT from an interior portion of an eye of a patient. At step 404, a second command may be sent to an OCT scanner to initiate binocular en face OCT via a surgical microscope and an ophthalmic lens, the surgical microscope and the ophthalmic lens also used to generate an optical image of the interior portion of the eye, and the surgical microscope including a left ocular and a right ocular. At step 406, right scan data and left scan data may be received from the OCT scanner. At step 408, a left en face image may be generated from the left scan data and a right en face image may be generated from the right scan data. At step 410, the left en face image is caused to be displayed in the left ocular and the right en face image is caused to be displayed in the right ocular.

Figure 5:
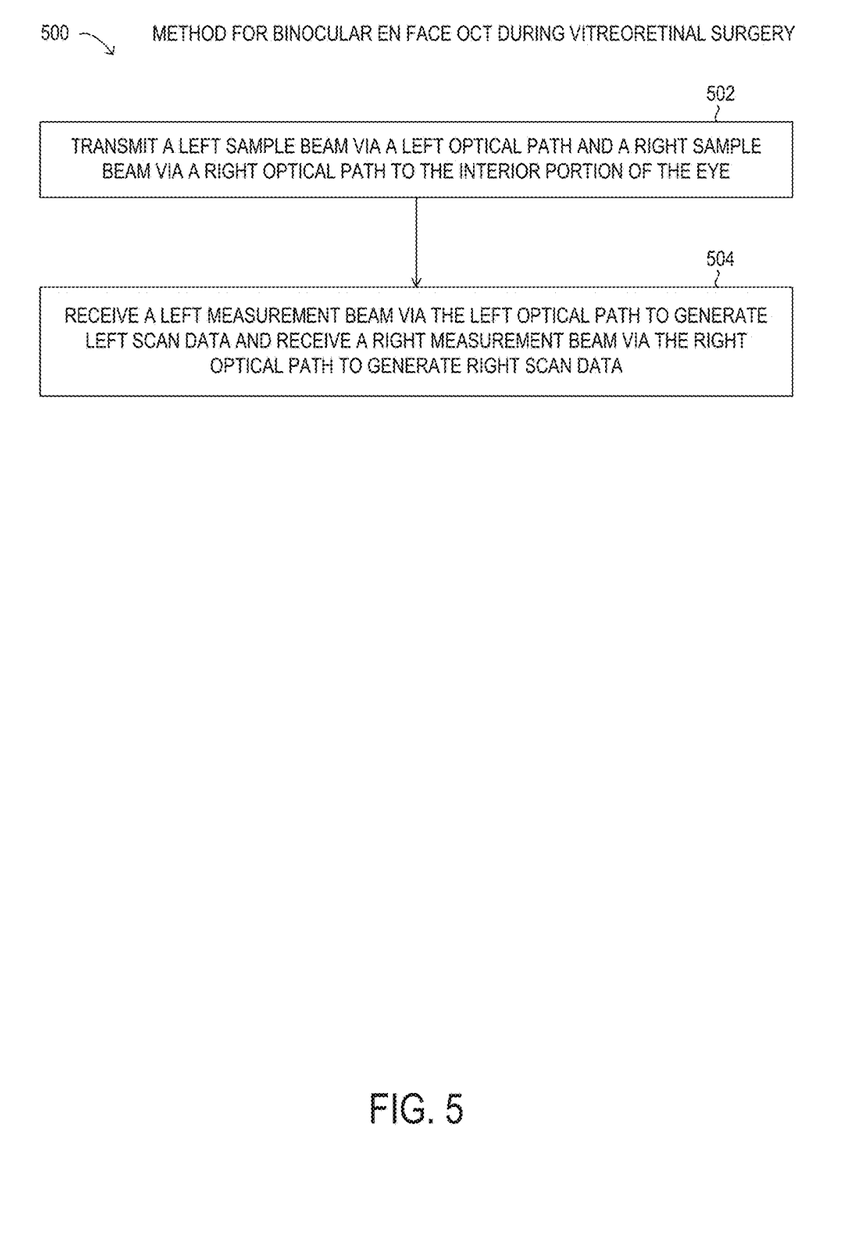
FIG. 5 is a flow chart of selected elements of a method for binocular en face OCT during vitreoretinal surgery.

Referring now to FIG. 5, a flow chart of selected elements of an embodiment of a method 500 for binocular en face OCT imaging during vitreoretinal surgery, as described herein, is depicted. Method 500 describes steps and procedures that OCT scanner 134 and 135 may perform while a user operates surgical microscopy scanning instruments 100 and 200 to view the fundus of an eye and performs surgical procedures based on the view of the fundus. It is noted that certain operations described in method 500 may be optional or may be rearranged in different embodiments. Method 500 may be performed in conjunction with method 400 in FIG. 4.

Method 500 may begin, at step 502, by transmitting a left sample beam via a left optical path and a right sample beam via a right optical path to the interior portion of the eye. As noted, the left and right sample beams may be temporally modulated or may be transmitted simultaneously, as described with respect to surgical microscopy instruments 100 and 200. At step 504, a left measurement beam may be received via the left optical path to generate left scan data and a right measurement beam may be received via the right optical path to generate right scan data. The left and right scan data may then be sent to OCT scanning controller 150 and 151, as described above.

As disclosed herein, binocular en face OCT imaging during ophthalmic surgery may be performed with an OCT scanning controller that interfaces to an OCT scanner used with a surgical microscope. The OCT scanner may generate left and right sample beams, and receive left and right measurement beams, respectively, to generate left and right scan data. The OCT scanning controller may process the left and right scan data to generate left and right en face images for respective viewing from binoculars in the surgical microscope to obtain an intraoperative stereoscopic en face view of interior portions of the eye.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method for performing ophthalmic surgery, the method comprising: receiving, by an optical coherence tomography (OCT) scanning controller coupled to a surgical microscope, a command indicating binocular en face viewing of the interior portion of an eye of a patient, wherein the surgical microscope is used for viewing the interior portion of the eye using an ophthalmic lens and used for generating an optical image of the interior portion of the eye, wherein the surgical microscope includes a left ocular receiving first light via a left optical path and a right ocular receiving second light via a right optical path, and wherein the OCT scanning controller is in communication with an OCT scanner; transmitting, by the OCT scanner, a left sample beam via the left optical path and a right sample beam via the right optical path to the interior portion of the eye; receiving, by the OCT scanner, a left measurement beam via the left optical path to generate left scan data; receiving, by the OCT scanner, a right measurement beam via the right optical path to generate right scan data; receiving, by the OCT scanning controller, the right scan data and the left scan data from the OCT scanner; generating a left en face image from the left scan data; generating a right en face image from the right scan data; causing the left en face image to be displayed in the left ocular; and causing the right en face image to be displayed in the right ocular;
wherein the right en face image and the left en face image exhibit angular diversity with respect to the interior portion of the eye; and
wherein the right en face image and left en face image are viewable together to visualize a 3-dimensional (3D) en face view with a selected depth or a selected tissue layer.

2. The method of claim 1, wherein the transmitting further comprises:
reciprocating, by the OCT scanner, an optical mirror from a common optical source to generate the left sample beam and the right sample beam in an alternating manner in time.

3. The method of claim 2, wherein the receiving, by the OCT scanner, the left measurement beam and the receiving, by the OCT scanner, the right measurement beam further comprises:
receiving, by the OCT scanner, the left measurement beam and the right measurement beam in the alternating manner in time.

4. The method of claim 1, wherein the transmitting further comprises:
splitting, by the OCT scanner, light from a common optical source to simultaneously transmit the left sample beam and the right sample beam.

5. The method of claim 4, wherein the receiving, by the OCT scanner, the left measurement beam and the receiving, by the OCT scanner, the right measurement beam further comprises:
receiving, by the OCT scanner, the left measurement beam using a first detector; and
receiving, by the OCT scanner, the right measurement beam using a second detector.

6. The method of claim 1, wherein the right en face image and the left en face image exhibit angular diversity with respect to the interior portion of the eye.

7. The method of claim 1, wherein the right en face image and the left en face image are viewable together to visualize a 3-dimensional (3D) en face view.

8. The method of claim 7, wherein the 3D en face view depicts a selected depth from the left scan data and the right scan data.

9. The method of claim 7, wherein the 3D en face view depicts a selected tissue layer from the left scan data and the right scan data.

10. An optical coherence tomography (OCT) scanning controller for binocular en face OCT imaging during ophthalmic surgery, the OCT scanning controller comprising: a processor having access to memory media storing instructions executable by the processor for: receiving a first command for binocular en face OCT from an interior portion of an eye of a patient; sending a second command to an OCT scanner to initiate binocular en face OCT via a surgical microscope and an ophthalmic lens, wherein the surgical microscope and the ophthalmic lens are also used to generate an optical image of the interior portion of the eye, and wherein the surgical microscope includes a left ocular receiving first light via a left optical path and a right ocular receiving second light via a right optical path, the OCT scanner enabled for: transmitting a left sample beam via the left optical path and a right sample beam via the right optical path to the interior portion of the eye; receiving a left measurement beam via the left optical path to generate left scan data; and receiving a right measurement beam via the right optical path to generate right scan data; the memory media further storing instructions for: receiving the right scan data and the left scan data from the OCT scanner; generating a left en face image from the left scan data; generating a right en face image from the right scan data; causing the left en face image to be displayed in the left ocular; and causing the right en face image to be displayed in the right ocular;
wherein the right en face image and the left en face image exhibit angular diversity with respect to the interior portion of the eye; and wherein the right en face image and left en face image are viewable together to visualize a 3-dimensional (3D) en face view with a selected depth or a selected tissue layer.

11. The OCT scanning controller of claim 10, wherein the transmitting further comprises the OCT scanner enabled for:
   reciprocating an optical mirror from a common optical source to generate the left sample beam and the right sample beam in an alternating manner in time.

12. The OCT scanning controller of claim 11, wherein the receiving the left measurement beam and the receiving the right measurement beam further comprises the OCT scanner enabled for:
   receiving the left measurement beam and the right measurement beam in the alternating manner in time.

13. The OCT scanning controller of claim 10, wherein the transmitting further comprises the OCT scanner enabled for:
   splitting light from a common optical source for simultaneously transmitting the left sample beam and the right sample beam.

14. The OCT scanning controller of claim 13, wherein the receiving the left measurement beam and the receiving the right measurement beam further comprises the OCT scanner enabled for:
   receiving the left measurement beam using a first detector; and
   receiving the right measurement beam using a second detector.

15. The OCT scanning controller of claim 10, wherein the right en face image and the left en face image exhibit angular diversity with respect to the interior portion of the eye.

16. The OCT scanning controller of claim 11, wherein the right en face image and the left en face image are viewable together to visualize a 3-dimensional (3D) en face view.

17. The OCT scanning controller of claim 16, wherein the 3D en face view depicts a selected depth from the left scan data and the right scan data.

18. The OCT scanning controller of claim 16, wherein the 3D en face view depicts a selected tissue layer from the left scan data and the right scan data.

* * * * *